United States Patent [19]

Pissiotas et al.

[11] Patent Number: 5,049,181
[45] Date of Patent: Sep. 17, 1991

[54] NOVEL HERBICIDALLY ACTIVE N-PHENYL-AZOLES

[75] Inventors: Georg Pissiotas, Lörrach, Fed. Rep. of Germany; Hans Moser, Magden; Hans-Georg Brunner, Lausen, both of Switzerland

[73] Assignee: Ciba-Geigy Corporation, Ardsley, N.Y.

[21] Appl. No.: 440,007

[22] Filed: Nov. 21, 1989

[30] Foreign Application Priority Data

Nov. 25, 1988 [CH] Switzerland ............... 4384/88

[51] Int. Cl.$^5$ ............. C07D 231/54; C07D 401/10; C07D 403/10; C07D 413/10
[52] U.S. Cl. ...................................... 71/90; 71/92; 544/117; 544/127; 544/133; 544/139; 544/140; 544/236; 546/271; 546/121; 548/181; 548/262.4; 548/266.4; 548/302; 548/336; 548/369; 548/374; 548/375; 548/376; 548/377; 548/378
[58] Field of Search ............ 548/369, 181, 266.4, 548/336; 71/92, 90; 544/140; 546/271

[56] References Cited

U.S. PATENT DOCUMENTS

| | | | |
|---|---|---|---|
| 4,108,628 | 8/1978 | Wolf | 548/369 |
| 4,608,080 | 8/1986 | Haga et al. | 548/369 |
| 4,624,699 | 11/1986 | Nagano et al. | 548/369 |
| 4,695,312 | 9/1987 | Hayase et al. | 548/369 |
| 4,752,325 | 6/1988 | Haga et al. | 548/369 |
| 4,946,492 | 8/1990 | Pissiotas et al. | 71/72 |

OTHER PUBLICATIONS

Futatsuya et al., Chemical Abstracts, vol. 103, No. 196075 (1985).
Davis et al., Chem. Abstr. 112:098378 (1990).
Stanik et al., Chem. Abstr. 111:042668 (1989).

Primary Examiner—Mukund J. Shah
Assistant Examiner—E. Bernhardt
Attorney, Agent, or Firm—Kevin T. Mansfield; Edward McC. Roberts

[57] ABSTRACT

The invention relates to novel phenyl substituted pyrazoles, 4,5,6,7-tetrahydro-indazoles, 2,4,5,6-tetrahydrocyclopenta[c]pyrazoles, octahydroimidazo[1,5-a]pyridin-1,3-diones, hexahydro-1H-pyrrolo[1,2-c]-imidazol-1,3-diones, hexahydro-1H-1,2,4-triazolo[1,2-a]pyridazin-1,3-diones and tetrahydro-1H,5H-pyrazolo[1,2-a][1,2,4]triazol-1,3-diones which have phenyl-substituted in the 2-position, herbicidal activity. It furthermore relates to agrochemical compositions, which contain these compounds, to their use for controlling undesirable plant-growth and for processes for the preparation of the compounds according to this invention.

The novel N-Phenyl-azoles correspond to the formula I

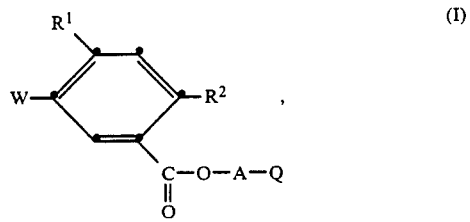

wherein

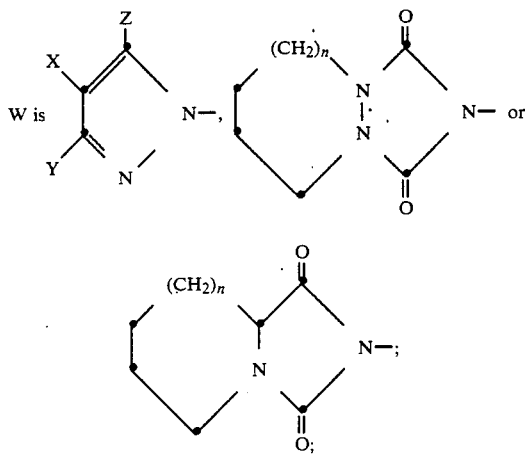

$R^1$ is hydrogen or halogen;
$R^2$ is halogen;
A is a straight-chain or branched $C_1$-$C_4$-alkylene chain;
n is zero or 1;
Q is $-S(O)_m-R^3$; di-$C_1$-$C_4$-alkylamino; a 5- or 6-membered heterocyclus, that is bound via a carbon or nitrogen atom and which contains 1 to 3 heteroatoms selected from the group consisting of N, O and S, which heterocycles can be fused to a benzene ring and mono- or disubstituted by halogen, $C_1$-$C_4$-alkyl, $C_1$-$C_3$-haloalkyl, $C_1$-$C_3$-alkoxy, $C_1$-$C_3$-haloalkoxy, $C_1$-$C_3$-dialkylamino, hydroxy or carboxyl;
$R^3$ is $C_1$-$C_{10}$-alkyl;

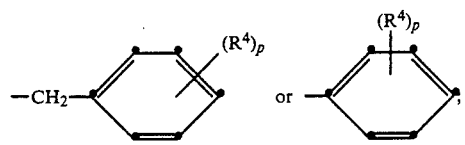

m is zero, 1 or 2;
$R^4$ is $C_1$-$C_4$-alkyl, halogen or $C_1$-$C_4$-alkoxy;
p is zero 1, 2, or 3;
X is hydrogen, halogen or $C_1$-$C_4$-alkyl;
Y is $C_1$-$C_4$-alkyl; or
X and Y form together a $-(CH_2)_q$-chain, which is optionally mono- or disubstituted by methyl;
q is three or four; and
Z is halogen, methyl, $C_1$-$C_6$-alkoxy or $C_1$-$C_6$-alkylthio; under inclusion of the salts of these azoles with acids, bases and complex-building substances.

16 Claims, No Drawings

NOVEL HERBICIDALLY ACTIVE N-PHENYL-AZOLES

The present invention relates to novel phenyl substituted pyrazoles, 4,5,6,7-tetrahydro-indazoles, Z,4,5,6-tetrahydro-cyclopenta[c]pyrazoles, octahydroimidazo[1,5-a]pyridin-1,3-diones, hexahydro-1H-pyrrolo[1,2-c]imidazol-1,3-diones, hexahydro-1H-1,2,4-triazolo[1,2-a]pyridazin-1,3-diones and tetrahydro-1H,5H-pyrazolol[1,2-a][1,2,4]triazol-1,3'-diones, which are phenyl-substituted in the 2-position and have herbicidal activity. It furthermore relates to agrochemical compositions, which contain these compounds, to their use for controlling undesirable plant-growth and for processes for the preparation of the compounds according to this invention.

The novel N-Phenyl-azoles correspond to the formula I

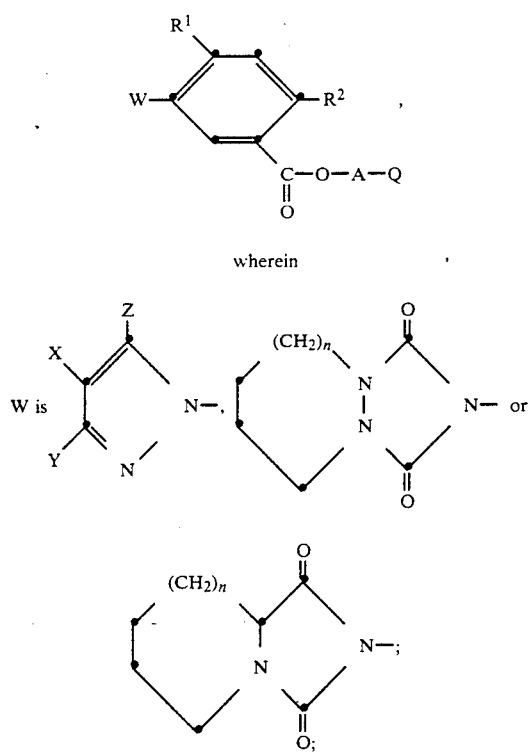

wherein $R^1$ is hydrogen or halogen;
$R^2$ is halogen;
A is a straight-chain or branched $C_1$–$C_4$-alkylene chain;
n is zero or 1;
Q is —$S(O)_m$—$R^3$; di-$C_1$–$C_4$-alkylamino; a 5- or 6-membered heterocycle, that is bound via a carbon or nitrogen atom and which contains 1 to 3 heteroatoms selected from the group consisting of N, O and S, which heterocycles can be fused to a benzene ring and be mono- or disubstituted by halogen, $C_1$–$C_4$-alkyl, $C_1$–$C_3$-haloalkyl, $C_1$–$C_3$-alkoxy, $C_1$–$C_3$-haloalkoxy, $C_1$–$C_3$-dialkylamino, hydroxy or carboxyl;
$R^3$ is $C_1$–$C_{10}$-alkyl;

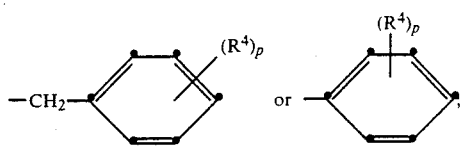

m is zero, 1 or 2;
$R^4$ is $C_1$–$C_4$-alkyl, halogen or $C_1$–$C_4$-alkoxy;
p is zero 1, 2, or 3;
X is hydrogen, halogen or $C_1$–$C_4$-alkyl;
Y is $C_1$–$C_4$-alkyl; or
X and Y form together a —$(CH_2)_q$-chain, which is optionally mono- or disubstituted by methyl;
q is three or four; and
Z is halogen, methyl, $C_1$–$C_6$-alkoxy or $C_1$–$C_6$-alkylthio; under inclusion of the salts of these azoles with acids, bases and complex-building substances.

The significations of the elements W, $R^1$ to $R^4$, A, n, Q, m, p, X, Y and Z, which are separated by a comma are to be considered as sub-group of these substituents. The invention also comprises scopes, which can be obtained by deletion of one or of several of the sub-groups of the definitions given under Formula I in the most generic and in preferred and most preferred ranges.

The definitions, used in this disclosure comprise the generic term as indicated but also those substituents, which can be obtained by combination of single substituents, e.g. the following specific single substituent, whereby this enumeration is not limiting the invention:

Halogen: Fluorine, chlorine, bromine and iodine, preferably fluorine and chlorine. Preferred $R^1$ is fluorine and chlorine and preferred $R^2$ is chlorine and bromine.

A as $C_1$–$C_4$-alkylene-chain is methano, ethano (ethan-1,2-diyl), 1-methylethano, 2-methylethano, propano (propane-1,3-diyl), 1-methylpropano, 2-methylpropano, 3-methylpropano, butano and ethane-1,1-diyl. Preferred are besides ethano those alkylene chains, which are branched in the vicinal position to the oxygen, such as 1-methylethano or 1-ethylethano, especially ethano and 1-methylethano.

Q as —$S(O)_m$—$R^3$ radical can be a thioether (m=zero), a $R^3$-sulfinylradical (m=1) or a $R^3$-sulfonylradical (m=2).

When $R^3$ is alkyl, the thioethers are preferred. If $R^3$ is an optionally substituted benzyl or phenyl radical, then are preferred beside the thioethers the sulfonyl (m =2) structures.

Dialkylamino is e.g. dimethylamino, methylethylamino, diethylamino, di-butylamino and di-isopropylamino.

A heterocyclic radical Q can be unsaturated as well as partially or also completely saturated and represent especially pyridin-2-yl, 1,3-thiazol5-yl, thiophen-2-yl, pyrrolidin-2-on-1-yl, pyrrolidin-1-yl, morpholin4-yl, furan-2-yl, indol-1-yl, pyrrol-1-yl, imidazol-1-yl, pyrazol-1-yl and 1,2,4-triazol-1-yl. These heterocycles can be substituted, such as e.g. 1-methylpyrazol-4-yl, 5-methylfuran-2-yl, 4-methyl-1,3-thiazol-5-yl or pyrrolidin-2- or -1-yl.

Alkyl is e.g. methyl, ethyl, isopropyl, n-propyl, n-butyl, isobutyl, sec.butyl, tert.butyl as well as the diverse isomeric pentyl-, hexyl-, heptyl-, octyl-, nonyl- and decyl-radicals.

Haloalkyl is e.g. fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; especially trichloromethyl, difluorochloromethyl, trifluoromethyl and dichlorofluoromethyl.

Alkoxy is e.g. methoxy, ethoxy, propoxy, isopropoxy, n-butoxy, isobutoxy, sec.butoxy and tert.butoxy; especially methoxy.

Haloalkoxy is e.g. fluoromethoxy, difluoromethoxy, trifluoromethoxy, 2,2,2-trifluoroethoxy, 2-fluoroethoxy, 2-chloroethoxy and 2,2,2-trichloroethoxy; especially difluoromethoxy, 2-chloroethoxy and trifluoromethoxy.

Alkylthio is e.g. methylthio, ethylthio, propylthio, isopropylthio, n-butylthio, isobutylthio, sec.butylthio or tert.butylthio; especially methylthio and ethylthio.

The substituent W in formula I can stand for diverse heterocyclic ring systems. In particular the following groups of compounds are meant:

Pyrazoles of the formula Ia

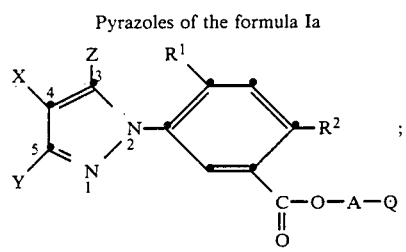

(Ia)

2,4,5,6-tetrahydro-cyclopenta[c]pyrazoles of the formula Ib

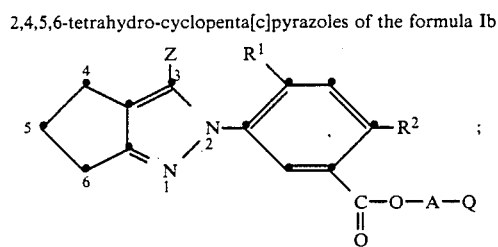

(Ib)

4,5,6,7-tetrahydro-indazoles of the formula Ic

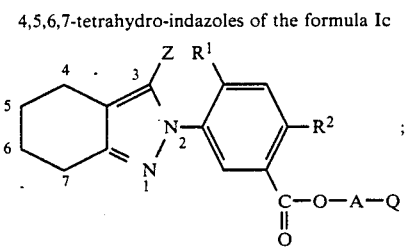

(Ic)

hexahydro-1H-pyrrolo[1,2-c]imidazol-1,3-diones of the formula Id

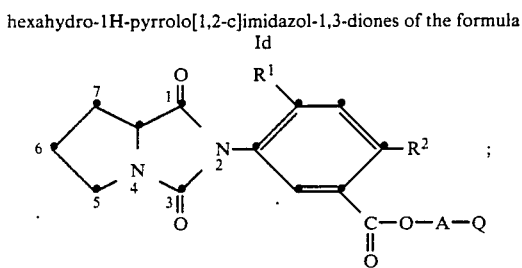

(Id)

octahydro-imidazo[1,5-a]pyridin-1,3-diones of the formula Ie

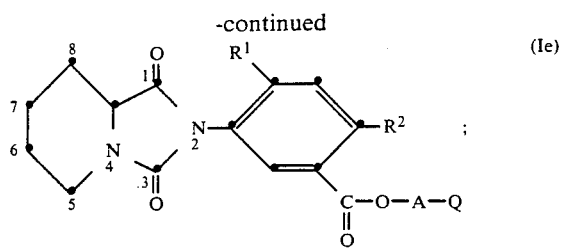

(Ie)

tetrahydro-1H,5H-pyrazolo[1,2-a][1,2,4]triazol-1,3-diones of the formula If

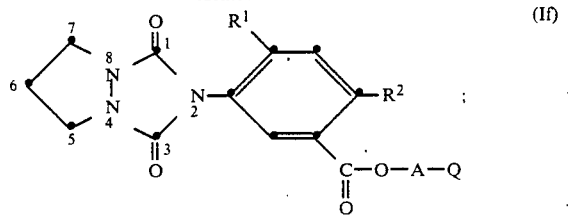

(If)

and hexahydro-1H-1,2,4-triazolo[1,2-a]pyridin-1,3-diones of the formula Ig

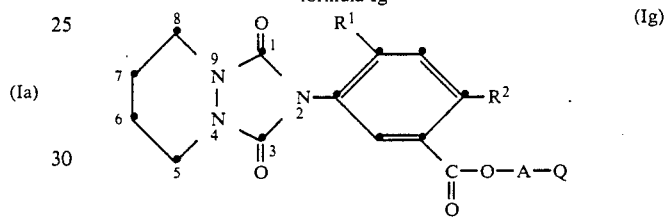

(Ig)

Preferred are the compounds of the formula I, wherein

W is as defined above;
$R^1$ is hydrogen, fluorine or chlorine;
$R^2$ is fluorine, chlorine or bromine;
A is a straight-chain or branched $C_2$–$C_4$-alkylene-chain;
n is zero or 1;
Q is $C_1$–$C_{10}$-alkylthio, —S(O)$_m R^3$, di-$C_1$–$C_4$-alkylamino, a heterocyclic radical, which is optionally mono- or disubstituted by $C_1$–$C_4$-alkyl or monosubstituted by a carboxyl radical and which is selected from the group consisting of pyridinyl, 1,3-thiazolyl, thiophenyl, pyrrolidinyl, morpholinyl, furanyl, indolyl, pyrazolyl, 1,2-oxazolyl, pyrrolyl, imidazolyl, pyrazolyl and 1,2,4-triazolyl;
$R^3$ is

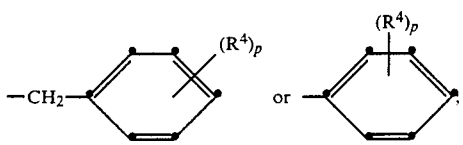

m is zero 1 or 2;
$R^4$ is $C_1$–$C_4$-alkyl, fluorine, chlorine, bromine or $C_1$–$C_4$-alkoxy;
p is 0, 1 or 2;
X is hydrogen, chlorine or bromine;
Y is $C_1$–$C_4$-alkyl; or
X and Y together form a —(CH$_2$)$_q$— chain;
q is 3 or 4; and
Z is chlorine, bromine, methyl, $C_1$–$C_6$-alkoxy or $C_1$–$C_6$-alkylthio.

Especially active are the compounds of the formula I, wherein
W is as defined before;
R¹ is hydrogen, fluorine or chlorine;
R² is chlorine or bromine;
A is ethano, 1-methylethano, 2-methylethano or propano;
n is zero or 1;
Q is C₁–C₆-alkylthio, —S(O)ₘR³, pyridin-2-yl, 1,3-thiazol-5-yl, thiophen-2-yl, pyrrolidin-2-on-1-yl, pyrrolidin-1-yl, morpholin-1-yl, furan-2-yl, indol-1-yl, pyrrol-1-yl. imidazol-1 yl, pyrazol-1-yl, 1,2,4-triazol-1-yl, 4-methyl-1,3-thiazol-5-yl or 5-methyl-furan-2-yl;
R³ is benzyl or phenyl;
m is zero, 1 or 2;
X and Y form together a —(CH₂)₄— chain; and
Z is chlorine or methyl.
Preferred are those compounds of formula I, wherein

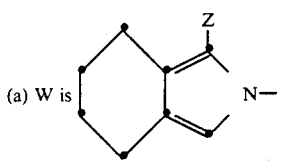

(a) W is wherein Z is chlorine or methyl;

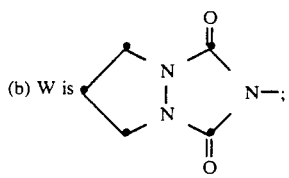

(b) W is

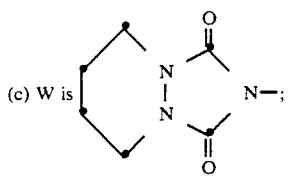

(c) W is

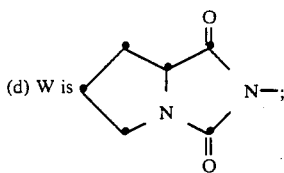

(d) W is

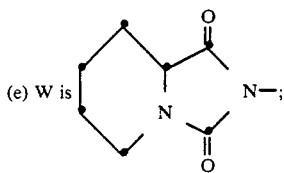

(e) W is f) A is —CH₂—CH₂—;

(g) A is —CH—CH₂—;
         |
         CH₃

(h) A is —CH₂—CH—;
              |
              CH₃ i) Q is C₁–C₆-alkylthio;
j) Q is di-C₁–C₄-alkylamino;
k) R¹ is fluorine and
R² is chlorine or bromine;
l) R¹ is fluorine and
R² is chlorine.

In consideration of their good herbicidal activity the compounds, which correspond to the following combinations of previously mentioned particular features, are especially pointed out:

m) the combination of the characteristics b), f), g), und i)
n) the combination of the characteristics b), f), g), und i)
o) the combination of the characteristics c), f), g), und i)
p) the combination of the characteristics d), f), g), und i)
q) the combination of the characteristics e), f), g), und i)

Especially good activity have the compounds of the formula I, wherein

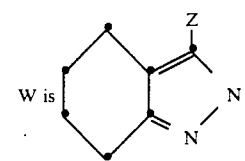

W is

Z is chlorine or methyl;

A is —CH₂—CH₂—; or —CH—CH₂—;
                        |
                        CH₃

Q is C₁–C₆-alkylthio;
R¹ is fluorine and
R² is chlorine or bromine.

Compounds to be named are especially
3-chloro-2-{4-chloro-2-fluoro-5-[1-methyl-2-(1-methylethylthio)-ethoxycarbonyl]-phenyl}-4,5,6,7-tetrahydro-2H-indazole,
3-chloro-2-[4-chloro-2-fluoro-5-(1-dimethylamino-1-methylethoxycarbonyl)phenyl]-4,5,6,7-tetrahydro-1H-indazole and
3-chlor-2-[4-chloro-2-fluoro-5-(2-ethylthio-1-methylethoxycarbonyl)phenyl]-4,5,6,7-tetrahydro-2H-indazole.

The compounds of the formula I can be prepared by
a) esterification of a carbonic acid derivative of the formula II, wherein R¹, R² and W are as defined above and R⁵ is hydroxyl, chlorine or bromine, with an alcohol of the formula III, wherein A and Q are as defined above

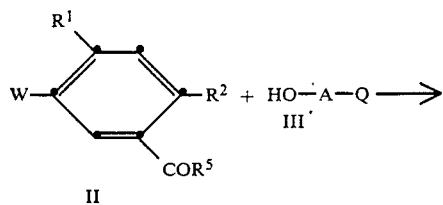

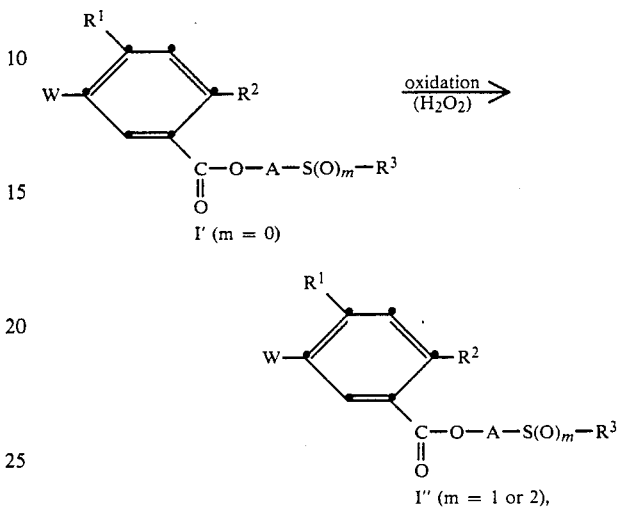

The starting material of the formulae II and III are known or can be produced in analogy to processes known from the literature.

The carbonic acid derivatives of the formula II, necessary for the synthesis of the pyrazoles, indazoles respectively cyclopenta[c]pyrazoles of the formulae Ia, Ib respectively Ic are described in the published European Patent application EP-A-0,138,527.

EP-A-0,104,532 relates to pyrrolo[1,2-c]imidazol-1,3-diones and imidazo[1,5-a]pyridin-1,3-diones of the formula II, which can be used as starting material for the production of the compounds of formula Id and Ie.

EP-A-0,104,484 further discloses pyrazol-[1,2-a][1,2,4]triazol-1,3-diones and 1,2,4-triazolo[1,2-a]pyrazidin-1,3-diones of the formula II, which can be used in the process according to the invention as starting material for the production of the end-products of the formulae If and Ig.

Processes for the production of the starting material of formula II are also disclosed in the European Patent Application No. 89810438.8.

The published European Patent applications EP-A-0,104,538 and EP-A-0,104,484 relate predominantly to simple esters of the formula II ($R^5$ is optionally substituted alkoxy). From these ester can be prepared, e.g. by saponification, optionally followed by chlorination or bromination (e.g. with $POCl_3$ or $POBr_3$) the free carbonic acid ($R^5$=OH) or the acid chlorides respectively bromides ($R^5$=Cl or Br) of the formula II.

The esterification reactions according to the invention are processes known to the skilled in the art.

The condensation of the acid chlorides respectively acid bromides of formula II with the alcohols of the formula III is advantageously conducted in a solvent that is inert to the reaction, at a temperature ranging from 0° C. to the boiling point of the solvent, especially until about 120° C. Thereby it can be advantageous to use bases, which bind the liberated HCl respectively HBr.

It is also possible to esterify directly the free carbonic acids of the formula II ($R^5$=OH) Then water-splitting resp. water-binding agents are needed. Water-splitting acids are e.g. protonic acids. As water-binding agents are to be mentioned especially carbodiimides, such as cyclohexyl carbodiimide.

The reaction-processes, starting from the carbonic acids of the formula II are also conducted advantageously in a solvent which is inert to the reaction, at temperatures of from 0° C. and about 100° C.

If the carbodiimide method is used, low temperatures of from 0° C. to about room temperature are preferred.

The compounds of the formula I″, wherein W, $R^1$, $R^2$, $R^3$ and A are as defined above and Q is —$S(O)_m$-$R^3$ and m is 1 or 2, can be prepared by oxidation of the thioesters of the formula I′ wherein W, $R^1$, $R^2$, $R^3$ and A is as defined above and m is zero.

These oxidations are preferably conducted in solvents at temperatures of from 0° C. to 100° C.

Such oxidations are known to the skilled in the art. They are described among other in Houben Weyl, "Methoden der Organischen Chemie" Vol. IX, page 211 ff. Appropriate oxidation agents are hydrogenperoxide or peracids such as e.g. m-chloroperbenzoic acid or potassium permanganate in glacial acetic acid e.g. analogous to J. Am. Chem. Soc. 63 (1941) p. 1971 or Can. J. Chem. 57 (1979) p. 2426.

The compounds of formula I are highly active active ingredients for plants that at suitable rates of application are excellently suitable as selective herbicides for controlling weeds in crops of useful plants. That is to say, at such rates of application the active ingredients of formula I are distinguished by a good selective herbicidal property against weeds. Culture plants, such as rye, barley, oats, wheat and maize, sorghum, rice, cotton and soybeans remain virtually undamaged at low rates of application. At increased rates of application the growth of the crop plants is influenced only to a small extent. If the rates of application are very high, the substances of formula I have total herbicidal properties.

The selective herbicidal activity of the compounds of the invention is observed both in pre-emergence and post-emergence application. These compounds can therefore be used with equal success pre- or post-emergence in selective weed control. The compounds of this invention are suited especially for pre-emergent application in the following crops: barley, wheat, maize, rice, sorghum, soya, cotton and sun-flowers and for post-emergent application in the following cultures: barley, wheat, maize, rice and sorghum.

Advantageously, the compounds or compositions of the invention can be applied also to the propagation material of the crop plant. Seed dressing, especially, may be mentioned here. Propagation material is seeds, plantlets or other parts of the plant from which the crop plants can be reared. The invention also relates to the propagation material treated with an effective amount of a compound of formula I.

The invention relates also to herbicidal compositions that contain a novel compound of formula I, and to methods for pre-and post-emergence weed control.

The compounds of formula I are used in unmodified form or, preferably, in the form of compositions together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant or extender, are prepared in known manner, e.g. by homogeneously mixing and/or grinding the active ingredients with extenders, e.g. solvents, solid carriers and, where appropriate, surface-active compounds (surfactants).

Suitable solvents or extenders are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids.

These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Surfactants customary in the art of formulation are described, inter alia, in the following publications:

"1986 International Mc Cutcheon's Emulsifiers and Detergents", Glen Rock, N.J., USA, 1986; H. Stache "Tensid Taschenbuch", 2nd edition, C. Hanser Verlag, Munich/Vienna, 1981; M. and J. Ash. "Encyclopedia of Surfactants", Vol. I-III, Chemical Publishing Co., N.Y., 1980-1981.

The active ingredient preparations usually contain 0.1 to 95 %, preferably 0.1 to 80%, of a compound of formula I, 1 to 99.9% of one or more solid or liquid adjuvants, and 0 to 25% of a surfactant.

Preferred formulations are composed especially as follows (throughout, percentages are by weight)

| Emulsifiable concentrates: | | |
|---|---|---|
| active ingredient | 1 to 20%, | preferably 5 to 10% |
| surfactant | 5 to 30%, | preferably 10 to 20% |
| liquid carrier | 50 to 94%, | preferably 70 to 85%. |
| Dusts: | | |
| active ingredient | 0.1 to 10%, | preferably 0.1 to 1% |
| solid carrier | 99.9 to 90%, | preferably 99.9 to 99%. |
| Suspension concentrates: | | |
| active ingredient | 5 to 75%, | preferably 10 to 50% |
| water | 94 to 25%, | preferably 88 to 30% |
| surfactant | 1 to 40%, | preferably 2 to 30%. |
| Wettable powders: | | |
| active ingredient | 0.5 to 90%, | preferably 1 to 80% |
| surfactant | 0.5 to 20%, | preferably 1 to 15% |
| solid carrier | 5 to 95%, | preferably 15 to 90%. |
| Granulates: | | |
| active ingredient | 0.5 to 30%, | preferably 3 to 15% |
| solid carrier | 99.5 to 70%, | preferably 97 to 85%. |

Whereas commercial products will preferably be formulated as concentrates, the end user will normally employ dilute formulations. The formulations can be diluted to a concentration as low as 0.001 % active ingredient.

The compositions may also contain further additives such as stabilisers, antifoams, viscosity regulators, binders, tackifiers and also fertilisers or other active ingredients for obtaining special effects.

The following Examples illustrate the invention.

EXAMPLES

H.1.1. Production of 3-chloro-2-{4-chloro-2-fluoro-5 [1-methyl-2-(1-methylethyl thio)-ethoxycarbonyl]-phenyl}-4,5,67,7-tetrahydro-2H-indazole A solution of 3.5 g of 3-chloro-2-(4-chloro-2-fluoro-5-chlorocarbonylphenyl)-4,5,6,7-tetrahy dro-2H-indazole in 50 ml of toluene is added dropwise at room temperature to a stirred solution of 1.4 g of (1-methylethyl)thio-propan-2-ol and 1.5 ml of triethylamine in 50 ml of toluene. After everything is added, the reaction mixture is stirred for another 3 hours at room temperature. The triethylamine-hydrochloride is then filtered off and the filtrate is concentrated under vacuum.

Thus 3.1 g of the title-compound of the formula

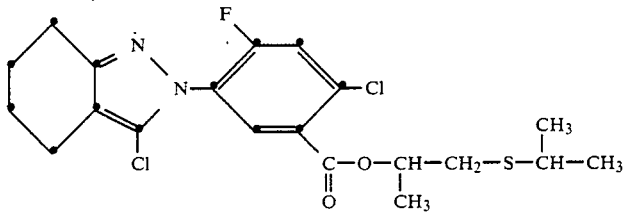

can be isolated as an oil with a refractory index $n_D^{24} = 1.5526$ (compound No. 1.05).

Analogously to the above example and the processes for production given in the disclosure, the compounds listed in tables 1 to 12 can be produced.

TABLE 1

Compounds of the formula

| Compound No. | A | Q | physical data |
|---|---|---|---|
| 1.01 | —CH—CH$_2$— | SCH$_3$ | |
| 1.02 | —CH—CH$_2$—<br>  \|<br>  CH$_3$ | SCH$_3$ | $n_D^{21}$ 1.5655 |
| 1.03 | —CH—CH$_2$—<br>  \|<br>  CH$_3$ | SC$_2$H$_5$ | $n_D^{24}$ 1.5538 |
| 1.04 | —CH—CH$_2$—<br>  \|<br>  CH$_3$ | SC$_3$H$_7$ | $n_D^{24}$ 1.5339 |
| 1.05 | —CH—CH$_2$—<br>  \|<br>  CH$_3$ | SC$_3$H$_7$(i) | $n_D^{24}$ 1.5526 |
| 1.06 | —CH—CH$_2$—<br>  \|<br>  CH$_3$ | SC$_4$H$_9$ | $n_D^{24}$ 1.5411 |

TABLE 1-continued

Compounds of the formula

[Structure: 4,5,6,7-tetrahydro-3-chloro-methyl-indazole linked via N to a phenyl ring bearing F, Cl, and C(=O)-O-A-Q]

| Compound No. | A | Q | physical data |
|---|---|---|---|
| 1.07 | $-CH(CH_3)-CH_2-$ | $SC_4H_9(s)$ | $n_D^{24}$ 1.5349 |
| 1.08 | $-CH(CH_3)-CH_2-$ | $SC_4H_9(t)$ | $n_D^{24}$ 1.5451 |
| 1.09 | $-CH(CH_3)-CH_2-$ | $SC_5H_{11}$ | |
| 1.10 | $-CH(CH_3)-CH_2-$ | $SC_6H_{13}$ | |
| 1.11 | $-CH(CH_3)-CH_2-$ | $SC_7H_{15}$ | |
| 1.12 | $-CH(CH_3)-CH_2-$ | $SC_8H_{17}$ | |
| 1.13 | $-CH(CH_3)-CH_2-$ | $SC_9H_{19}$ | |
| 1.14 | $-CH(CH_3)-CH_2-$ | $SC_{10}H_{21}$ | |
| 1.15 | $-CH(CH_3)-CH_2-$ | $SCH_2-C_6H_5$ (benzyl thioether) | |
| 1.16 | $-CH(CH_3)-CH_2-$ | $-S-C_6H_5$ (phenyl thioether) | |
| 1.17 | $-CH(CH_3)-CH_2-$ | $-N(CH_3)_2$ | $n_D^{24}$ 1.5603 |
| 1.18 | $-CH(CH_3)-CH_2-$ | $-N(C_2H_5)_2$ | $n_D^{25}$ 1.5458 |
| 1.19 | $-CH_2-CH_2-$ | 2,5-dimethyl-furan-3-yl | |
| 1.20 | $-CH_2-CH_2-$ | pyridyl | m.p.: 75-77° |

TABLE 1-continued

Compounds of the formula

[structure shown: bicyclic pyrazoline with Cl and CH₃ substituents linked via N-N to phenyl ring bearing F, Cl, and C(=O)-O-A-Q group]

| Compound No. | A | Q | physical data |
|---|---|---|---|
| 1.21 | —CH₂—CH₂— | 4-methylthiazol-2-yl (CH₃ on thiazole, S, N) | |
| 1.22 | —CH₂—CH₂— | thiophen-2-yl (S) | |
| 1.23 | —CH₂—CH₂— | 2-oxo-pyrrolidin-1-yl (—N, C=O) | |
| 1.24 | —CH₂—CH₂— | pyrrolidin-1-yl (—N) | |
| 1.25 | —CH₂—CH₂— | morpholin-4-yl (—N, O) | |
| 1.26 | —CH—CH₂—<br>   CH₃ | furan-2-yl (O) | |
| 1.27 | —CH₂—CH₂— | furan-2-yl (O) | |
| 1.28 | —CH—CH₂—<br>   CH₃ | indol-1-yl (N) | |
| 1.29 | —CH₂—CH₂— | pyrazol-1-yl (—N, N) | |
| 1.30 | —CH₂—CH₂— | pyrrol-1-yl (—N) | |

TABLE 1-continued
Compounds of the formula
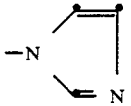
| Compound No. | A | Q | physical data |
|---|---|---|---|
| 1.31 | —CH$_2$—CH$_2$— |  | |
| 1.32 | —CH(CH$_3$)—CH$_2$— | 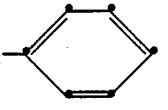 | |
| 1.33 | —CH(CH$_3$)—CH$_2$— | 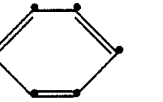 | |
| 1.34 | —CH(CH$_3$)—CH$_2$— | 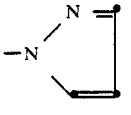 | |
| 1.35 | —CH$_2$—CH$_2$— | 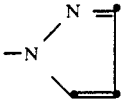 | |
| 1.36 | —CH(CH$_3$)—CH$_2$— | 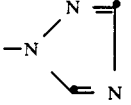 | |
| 1.37 | —CH(CH$_3$)—CH$_2$— | 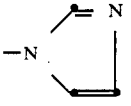 | |
| 1.38 | —CH(CH$_3$)—CH$_2$— | 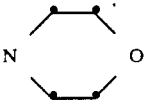 | |
| 1.39 | —CH(CH$_3$)—CH$_2$— | | |

TABLE 2

Compounds of the formula

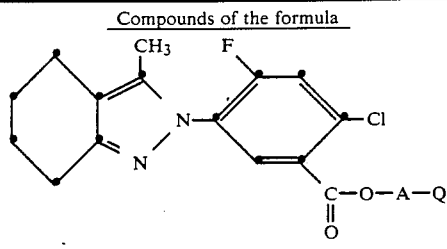

| Compound No. | A | Q | physical data |
|---|---|---|---|
| 2.01 | —CH₂CH₂— | —SCH₃ | |
| 2.02 | —CHCH₂— (CH₃) | —SCH₃ | |
| 2.03 | —CHCH₂— (CH₃) | —SC₂H₅ | |
| 2.04 | —CHCH₂— (CH₃) | —SC₃H₇(i) | |
| 2.05 | —CHCH₂— (CH₃) | —SC₄H₉ | |
| 2.06 | —CHCH₂— (CH₃) | —SC₄H₉(s) | |
| 2.07 | —CHCH₂— (CH₃) | —SC₄H₉(t) | |
| 2.08 | —CHCH₂— (CH₃) | —SC₈H₁₇ | |
| 2.09 | —CHCH₂— (CH₃) | —SCH₂—C₆H₅ | |
| 2.10 | —CHCH₂— (CH₃) | —N(CH₃)₂ | |
| 2.11 | —CH₂CH₂— | pyridyl | |
| 2.12 | —CH₂CH₂— | morpholino | |
| 2.13 | —CH₂CH₂— | furyl | |
| 2.14 | —CHCH₂— (CH₃) | imidazolyl | |
| 2.15 | —CHCH₂— (CH₃) | pyrazolyl | |
| 2.16 | —CHCH₂— (CH₃) | triazolyl | |
| 2.17 | —CHCH₂— (CH₃) | morpholino | |

TABLE 3

Compounds of the formula

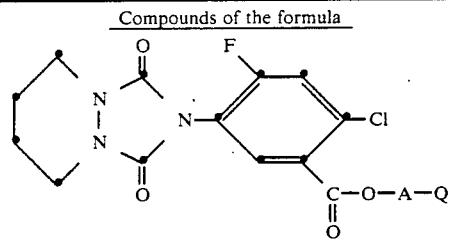

| Compound No. | A | Q | physical data |
|---|---|---|---|
| 3.01 | —CH₂CH₂— | —SCH₃ | |
| 3.02 | —CHCH₂— (CH₃) | —SCH₃ | |
| 3.03 | —CHCH₂— (CH₃) | —SC₂H₅ | |
| 3.04 | —CHCH₂— (CH₃) | —SC₃H₇(i) | |
| 3.05 | —CHCH₂— (CH₃) | —SC₄H₉ | |
| 3.06 | —CHCH₂— (CH₃) | —SC₄H₉(s) | |
| 3.07 | —CHCH₂— (CH₃) | —SC₄H₉(t) | |
| 3.08 | —CHCH₂— (CH₃) | —SC₈H₁₇ | |

TABLE 3-continued

Compounds of the formula:

[Structure: pyridazine-3,6-dione fused ring with N-N, attached to phenyl ring bearing F, Cl, and C(=O)-O-A-Q group]

| Compound No. | A | Q | physical data |
|---|---|---|---|
| 3.09 | —CH(CH$_3$)CH$_2$— | —SCH$_2$—(phenyl) | |
| 3.10 | —CH(CH$_3$)CH$_2$— | —N(CH$_3$)$_2$ | |
| 3.11 | —CH$_2$CH$_2$— | (pyridyl) | |
| 3.12 | —CH$_2$CH$_2$— | —N(morpholino)O | |
| 3.13 | —CH$_2$CH$_2$— | (furyl, O) | |
| 3.14 | —CH(CH$_3$)CH$_2$— | —N(imidazolyl) | |
| 3.15 | —CH(CH$_3$)CH$_2$— | —N(pyrazolyl) | |
| 3.16 | —CH(CH$_3$)CH$_2$— | —N(triazolyl) | |
| 3.17 | —CH(CH$_3$)—CH$_2$— | —N(morpholino)O | |

TABLE 4

Compounds of the formula:

[Structure: piperidine-2,6-dione type ring with N, attached to phenyl ring bearing F, Cl, and C(=O)-O-A-Q group]

| Compound No. | A | Q | physical data |
|---|---|---|---|
| 4.01 | —CH$_2$CH$_2$— | —SCH$_3$ | |
| 4.02 | —CH(CH$_3$)CH$_2$— | —SCH$_3$ | |
| 4.03 | —CH(CH$_3$)CH$_2$— | —SC$_2$H$_5$ | |
| 4.04 | —CH(CH$_3$)CH$_2$— | —SC$_3$H$_7$(i) | |
| 4.05 | —CH(CH$_3$)CH$_2$— | —SC$_4$H$_9$ | |
| 4.06 | —CH(CH$_3$)CH$_2$— | —SC$_4$H$_9$(s) | |
| 4.07 | —CH(CH$_3$)CH$_2$— | —SC$_4$H$_9$(t) | |
| 4.08 | —CH(CH$_3$)CH$_2$— | —SC$_8$H$_{17}$ | |
| 4.09 | —CH(CH$_3$)CH$_2$— | —SCH$_2$—(phenyl) | |
| 4.10 | —CH(CH$_3$)CH$_2$— | —N(CH$_3$)$_2$ | $n_D^{23}$ 1.5371 |
| 4.11 | —CH$_2$CH$_2$— | (pyridyl) | |
| 4.12 | —CH$_2$CH$_2$— | —N(morpholino)O | |
| 4.13 | —CH$_2$CH$_2$— | (furyl, O) | |
| 4.14 | —CH(CH$_3$)CH$_2$— | —N(imidazolyl) | |

TABLE 4-continued

Compounds of the formula

[Structure: pyrrolidine-dione fused system with N-phenyl group bearing F, Cl, and C(=O)-O-A-Q substituents]

| Compound No. | A | Q | physical data |
|---|---|---|---|
| 4.15 | -CHCH$_2$- with CH$_3$ | -N-N= (pyrazole ring) | |
| 4.16 | -CHCH$_2$- with CH$_3$ | -N-N= with N (triazole) | |
| 4.17 | -CH-CH$_2$- with CH$_3$ | -N   O (morpholine) | |

TABLE 5

Compounds of the formula

[Structure: pyrazolidine-3,5-dione with N-phenyl group bearing F, Cl, and C(=O)-O-A-Q substituents]

| Compound No. | A | Q | physical data |
|---|---|---|---|
| 5.01 | -CH$_2$CH$_2$- | -SCH$_3$ | |
| 5.02 | -CHCH$_2$- with CH$_3$ | -SCH$_3$ | |
| 5.03 | -CHCH$_2$- with CH$_3$ | -SC$_2$H$_5$ | |
| 5.04 | -CHCH$_2$- with CH$_3$ | -SC$_3$H$_7$(i) | |
| 5.05 | -CHCH$_2$- with CH$_3$ | -SC$_4$H$_9$ | |
| 5.06 | -CHCH$_2$- with CH$_3$ | -SC$_4$H$_9$(s) | |
| 5.07 | -CHCH$_2$- with CH$_3$ | -SC$_4$H$_9$(t) | |
| 5.08 | -CHCH$_2$- with CH$_3$ | -SC$_8$H$_{17}$ | |

TABLE 5-continued

Compounds of the formula

[Structure: same as Table 5]

| Compound No. | A | Q | physical data |
|---|---|---|---|
| 5.09 | -CHCH$_2$- with CH$_3$ | -SCH$_2$-phenyl | |
| 5.10 | -CHCH$_2$- with CH$_3$ | -N(CH$_3$)$_2$ | |
| 5.11 | -CH$_2$CH$_2$- | pyridyl | |
| 5.12 | -CH$_2$CH$_2$- | -N   O (morpholine) | |
| 5.13 | -CH$_2$CH$_2$- | furyl (O) | |
| 5.14 | -CHCH$_2$- with CH$_3$ | imidazole | |
| 5.15 | -CHCH$_2$- with CH$_3$ | pyrazole | |
| 5.16 | -CHCH$_2$- with CH$_3$ | triazole | |
| 5.17 | -CH-CH$_2$- with CH$_3$ | -N   O (morpholine) | |

TABLE 6

Compounds of the formula

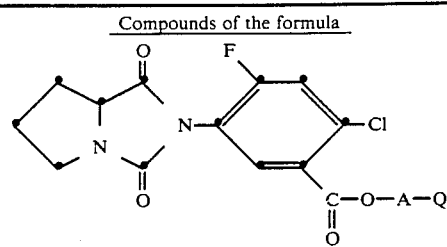

| Compound No. | A | Q | physical data |
|---|---|---|---|
| 6.01 | —CH$_2$CH$_2$— | —SCH$_3$ | |
| 6.02 | —CH(CH$_3$)CH$_2$— | —SCH$_3$ | |
| 6.03 | —CH(CH$_3$)CH$_2$— | —SC$_2$H$_5$ | |
| 6.04 | —CH(CH$_3$)CH$_2$— | —SC$_3$H$_7$(i) | |
| 6.05 | —CH(CH$_3$)CH$_2$— | —SC$_4$H$_9$ | |
| 6.06 | —CH(CH$_3$)CH$_2$— | —SC$_4$H$_9$(s) | |
| 6.07 | —CH(CH$_3$)CH$_2$— | —SC$_4$H$_9$(t) | |
| 6.08 | —CH(CH$_3$)CH$_2$— | —SC$_8$H$_{17}$ | |
| 6.09 | —CH(CH$_3$)CH$_2$— | —SCH$_2$-phenyl | |
| 6.10 | —CH(CH$_3$)CH$_2$— | —N(CH$_3$)$_2$ | |
| 6.11 | —CH$_2$CH$_2$— | pyridyl | |
| 6.12 | —CH$_2$CH$_2$— | morpholino | |
| 6.13 | —CH$_2$CH$_2$— | furyl | |
| 6.14 | —CH(CH$_3$)CH$_2$— | pyrazolyl | |

TABLE 6-continued

Compounds of the formula

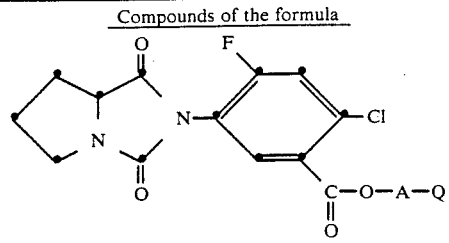

| Compound No. | A | Q | physical data |
|---|---|---|---|
| 6.15 | —CH(CH$_3$)CH$_2$— | pyrazolyl | |
| 6.16 | —CH(CH$_3$)CH$_2$— | triazolyl | |
| 6.17 | —CH(CH$_3$)CH$_2$— | morpholino | |

TABLE 7

Compounds of the formula

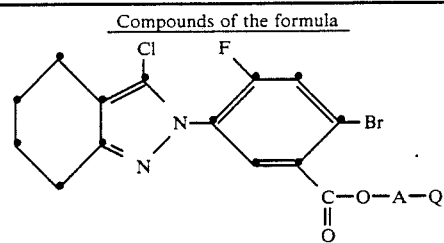

| Compound No. | A | Q | physical data |
|---|---|---|---|
| 7.01 | —CH$_2$CH$_2$— | —SCH$_3$ | |
| 7.02 | —CH(CH$_3$)CH$_2$— | —SCH$_3$ | |
| 7.03 | —CH(CH$_3$)CH$_2$— | —SC$_2$H$_5$ | |
| 7.04 | —CH(CH$_3$)CH$_2$— | —SC$_3$H$_7$(i) | |
| 7.05 | —CH(CH$_3$)CH$_2$— | —SC$_4$H$_9$ | |
| 7.06 | —CH(CH$_3$)CH$_2$— | —SC$_4$H$_9$(s) | |
| 7.07 | —CH(CH$_3$)CH$_2$— | —SC$_4$H$_9$(t) | |
| 7.08 | —CH(CH$_3$)CH$_2$— | —SC$_8$H$_{17}$ | |

TABLE 7-continued

Compounds of the formula

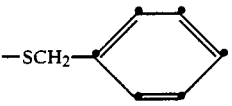

| Compound No. | A | Q | physical data |
|---|---|---|---|
| 7.09 | —CHCH₂— with CH₃ | —SCH₂—C₆H₅ (phenyl) | |
| 7.10 | —CHCH₂— with CH₃ | —N(CH₃)₂ | |
| 7.11 | —CH₂CH₂— | 2-methylpyridinyl | |
| 7.12 | —CH₂CH₂— | morpholino | |
| 7.13 | —CH₂CH₂— | furyl | |
| 7.14 | —CHCH₂— with CH₃ | imidazolyl | |
| 7.15 | —CHCH₂— with CH₃ | pyrazolyl | |
| 7.16 | —CHCH₂— with CH₃ | triazolyl | |
| 7.17 | —CH—CH₂— with CH₃ | morpholino | |

TABLE 8

Compounds of the formula

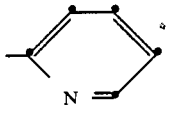

| Compound No. | A | Q | physical data |
|---|---|---|---|
| 8.01 | —CH₂CH₂— | —SCH₃ | |
| 8.02 | —CHCH₂— with CH₃ | —SCH₃ | |
| 8.03 | —CHCH₂— with CH₃ | —SC₂H₅ | |
| 8.04 | —CHCH₂— with CH₃ | —SC₃H₇(i) | |
| 8.05 | —CHCH₂— with CH₃ | —SC₄H₉ | |
| 8.06 | —CHCH₂— with CH₃ | —SC₄H₉(s) | |
| 8.07 | —CHCH₂— with CH₃ | —SC₄H₉(t) | |
| 8.08 | —CHCH₂— with CH₃ | —SC₈H₁₇ | |
| 8.09 | —CHCH₂— with CH₃ | —SCH₂—C₆H₅ (phenyl) | |
| 8.10 | —CHCH₂— with CH₃ | —N(CH₃)₂ | |
| 8.11 | —CH₂CH₂— | 2-methylpyridinyl | |
| 8.12 | —CH₂CH₂— | morpholino | |
| 8.13 | —CH₂CH₂— | furyl | |
| 8.14 | —CHCH₂— with CH₃ | imidazolyl | |

TABLE 8-continued

Compounds of the formula

[structure: methyl-pyrazole fused to cyclohexane, N-linked to fluoro-bromo-phenyl with C(O)-O-A-Q]

| Compound No. | A | Q | physical data |
|---|---|---|---|
| 8.15 | $-\underset{\underset{CH_3}{\vert}}{CH}CH_2-$ | pyrazolyl (-N-N=) |  |
| 8.16 | $-\underset{\underset{CH_3}{\vert}}{CH}CH_2-$ | triazolyl (-N-N=, N) |  |
| 8.17 | $-\underset{\underset{CH_3}{\vert}}{CH}-CH_2-$ | morpholinyl (-N O) |  |

TABLE 9

Compounds of the formula

[structure: pyridazine-3,6-dione fused to cyclohexane, N-linked to fluoro-bromo-phenyl with C(O)-O-A-Q]

| Compound No. | A | Q | physical data |
|---|---|---|---|
| 9.01 | $-CH_2CH_2-$ | $-SCH_3$ |  |
| 9.02 | $-\underset{\underset{CH_3}{\vert}}{CH}CH_2-$ | $-SCH_3$ |  |
| 9.03 | $-\underset{\underset{CH_3}{\vert}}{CH}CH_2-$ | $-SC_2H_5$ |  |
| 9.04 | $-\underset{\underset{CH_3}{\vert}}{CH}CH_2-$ | $-SC_3H_7(i)$ |  |
| 9.05 | $-\underset{\underset{CH_3}{\vert}}{CH}CH_2-$ | $-SC_4H_9$ |  |
| 9.06 | $-\underset{\underset{CH_3}{\vert}}{CH}CH_2-$ | $-SC_4H_9(s)$ |  |
| 9.07 | $-\underset{\underset{CH_3}{\vert}}{CH}CH_2-$ | $-SC_4H_9(t)$ |  |
| 9.08 | $-\underset{\underset{CH_3}{\vert}}{CH}CH_2-$ | $-SC_8H_{17}$ |  |
| 9.09 | $-\underset{\underset{CH_3}{\vert}}{CH}CH_2-$ | $-SCH_2-\text{phenyl}$ |  |
| 9.10 | $-\underset{\underset{CH_3}{\vert}}{CH}CH_2-$ | $-N(CH_3)_2$ |  |
| 9.11 | $-CH_2CH_2-$ | pyridyl |  |
| 9.12 | $-CH_2CH_2-$ | morpholinyl |  |
| 9.13 | $-CH_2CH_2-$ | furyl |  |
| 9.14 | $-\underset{\underset{CH_3}{\vert}}{CH}CH_2-$ | pyrazolyl |  |
| 9.15 | $-\underset{\underset{CH_3}{\vert}}{CH}CH_2-$ | pyrazolyl |  |
| 9.16 | $-\underset{\underset{CH_3}{\vert}}{CH}CH_2-$ | triazolyl |  |
| 9.17 | $-\underset{\underset{CH_3}{\vert}}{CH}-CH_2-$ | morpholinyl |  |

TABLE 10

Compounds of the formula

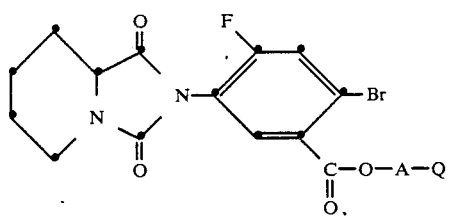

| Compound No. | A | Q | physical data |
|---|---|---|---|
| 10.01 | —CH$_2$CH$_2$— | —SCH$_3$ | |
| 10.02 | —CH(CH$_3$)CH$_2$— | —SCH$_3$ | |
| 10.03 | —CH(CH$_3$)CH$_2$— | —SC$_2$H$_5$ | |
| 10.04 | —CH(CH$_3$)CH$_2$— | —SC$_3$H$_7$(i) | |
| 10.05 | —CH(CH$_3$)CH$_2$— | —SC$_4$H$_9$ | |
| 10.06 | —CH(CH$_3$)CH$_2$— | —SC$_4$H$_9$(s) | |
| 10.07 | —CH(CH$_3$)CH$_2$— | —SC$_4$H$_9$(t) | |
| 10.08 | —CH(CH$_3$)CH$_2$— | —SC$_8$H$_{17}$ | |
| 10.09 | —CH(CH$_3$)CH$_2$— | —SCH$_2$—C$_6$H$_5$ | |
| 10.10 | —CH(CH$_3$)CH$_2$— | —N(CH$_3$)$_2$ | |
| 10.11 | —CH$_2$CH$_2$— | pyridyl | |
| 10.12 | —CH$_2$CH$_2$— | morpholino | |
| 10.13 | —CH$_2$CH$_2$— | furyl | |
| 10.14 | —CH(CH$_3$)CH$_2$— | pyrazolyl | |

TABLE 10-continued

Compounds of the formula

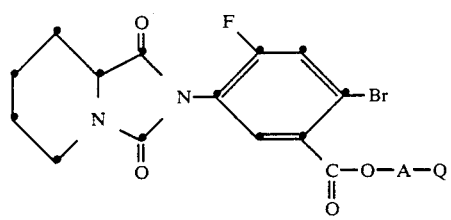

| Compound No. | A | Q | physical data |
|---|---|---|---|
| 10.15 | —CH(CH$_3$)CH$_2$— | pyrazolyl | |
| 10.16 | —CH(CH$_3$)CH$_2$— | triazolyl | |
| 10.17 | —CH(CH$_3$)CH$_2$— | morpholino | |

TABLE 11

Compounds of the formula

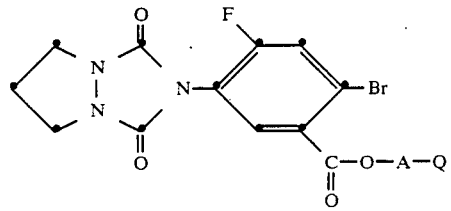

| Compound No. | A | Q | physical data |
|---|---|---|---|
| 11.01 | —CH$_2$CH$_2$— | —SCH$_3$ | |
| 11.02 | —CH(CH$_3$)CH$_2$— | —SCH$_3$ | |
| 11.03 | —CH(CH$_3$)CH$_2$— | —SC$_2$H$_5$ | |
| 11.04 | —CH(CH$_3$)CH$_2$— | —SC$_3$H$_7$(i) | |
| 11.05 | —CH(CH$_3$)CH$_2$— | —SC$_4$H$_9$ | |
| 11.06 | —CH(CH$_3$)CH$_2$— | —SC$_4$H$_9$(s) | |
| 11.07 | —CH(CH$_3$)CH$_2$— | —SC$_4$H$_9$(t) | |
| 11.08 | —CH(CH$_3$)CH$_2$— | —SC$_8$H$_{17}$ | |

TABLE 11-continued
Compounds of the formula

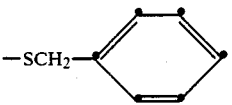

| Compound No. | A | Q | physical data |
|---|---|---|---|
| 11.09 | —CHCH₂— with CH₃ | —SCH₂—C₆H₅ | |
| 11.10 | —CHCH₂— with CH₃ | —N(CH₃)₂ | |
| 11.11 | —CH₂CH₂— | pyridyl | |
| 11.12 | —CH₂CH₂— | —N(morpholino) O | |
| 11.13 | —CH₂CH₂— | furyl (O) | |
| 11.14 | —CHCH₂— with CH₃ | imidazolyl | |
| 11.15 | —CHCH₂— with CH₃ | pyrazolyl | |
| 11.16 | —CHCH₂— with CH₃ | triazolyl | |
| 11.17 | —CH—CH₂— with CH₃ | morpholino | |

TABLE 12
Compounds of the formula

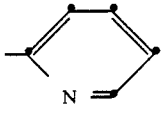

| Compound No. | A | Q | physical data |
|---|---|---|---|
| 12.01 | —CH₂CH₂— | —SCH₃ | |
| 12.02 | —CHCH₂— with CH₃ | —SCH₃ | |
| 12.03 | —CHCH₂— with CH₃ | —SC₂H₅ | |
| 12.04 | —CHCH₂— with CH₃ | —SC₃H₇(i) | |
| 12.05 | —CHCH₂— with CH₃ | —SC₄H₉ | |
| 12.06 | —CHCH₂— with CH₃ | —SC₄H₉(s) | |
| 12.07 | —CHCH₂— with CH₃ | —SC₄H₉(t) | |
| 12.08 | —CHCH₂— with CH₃ | —SC₈H₁₇ | |
| 12.09 | —CHCH₂— with CH₃ | —SCH₂—C₆H₅ | |
| 12.10 | —CHCH₂— with CH₃ | —N(CH₃)₂ | |
| 12.11 | —CH₂CH₂— | pyridyl | |
| 12.12 | —CH₂CH₂— | morpholino | |
| 12.13 | —CH₂CH₂— | furyl (O) | |
| 12.14 | —CHCH₂— with CH₃ | imidazolyl | |

TABLE 12-continued

Compounds of the formula

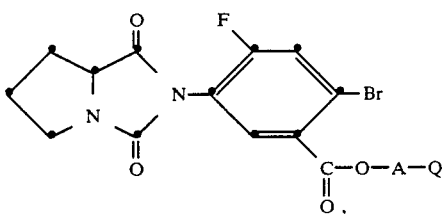

| Compound No. | A | Q | physical data |
|---|---|---|---|
| 12.15 | CH₃<br>\|<br>—CHCH₂— | —N⟨N=•⟩ | |
| 12.16 | CH₃<br>\|<br>—CHCH₂— | —N⟨N=•…N⟩ | |
| 12.17 | CH₃<br>\|<br>—CH—CH₂— | —N⟨ ⟩O | |

F. FORMULATION EXAMPLES

EXAMPLE F1

Formulation Examples for active ingredients of formula I (throughout, percentages are by weight)

| (a) Emulsifiable concentrates | (a) | (b) | (c) |
|---|---|---|---|
| a compound according to Table 1 to 12 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
|---|---|---|---|
| a compound according Table 1 to 12 | 80% | 10% | 5% |
| ethylene glycol monomethyl ether | 20% | — | — |
| polyethylene glycol MW 400 | — | 70% | — |
| N-methyl-2-pyrrolidone | — | 20% | 5% |
| epoxidised coconut oil | — | — | 90% |

These solutions are suitable for application in the form of micro-drops.

| (c) Granulates | (a) | (b) |
|---|---|---|
| a compound according to Table 1 to 12 | 5% | 10% |
| kaolin | 94% | — |
| highly dispersed silicic acid | 1% | — |
| attapulgite | — | 90% |

The active ingredient is dissolved, sprayed onto the carrier, and the solvent is subsequently evaporated off in vacuo.

| (d) Dusts | (a) | (b) | (c) |
|---|---|---|---|
| a compound according to Table 1 to 12 | 2% | 5% | 8% |
| highly dispersed silicic acid | 1% | 5% | 5% |
| talcum | 97% | — | 10% |
| kaolin | — | 90% | 77% |

Ready-for-use dusts are obtained by homogeneously mixing the carriers with the active ingredient.

| (e) Wettable powders | (a) | (b) |
|---|---|---|
| a compound according Table 1 to 12 | 20% | 60% |
| sodium lignosulfonate | 5% | 5% |
| sodium lauryl sulfate | 3% | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| a compound according to Table 1 to 12 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (g) Coated granulate | |
|---|---|
| a compound according to Table 1 to 12 | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound according to Table 1 to 12 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a aqueous emulsion | 75%<br>0.8% |
| water | 32% |

The finely ground active ingredient is intimately mixed with the adjuvants, giving a suspension concentrate from which suspensions of any desired concentration can be produced by dilution with water.

B. BIOLOGICAL EXAMPLES

EXAMPLE B1

Pre-emergence herbicidal action

In a greenhouse, immediately after sowing the test plants in seed trays the surface of the soil is treated with an aqueous dispersion of the test compound. An application rate of active ingredient/hectare of 4 kg/ha is tested. The seed trays are kept in the greenhouse at 22°-25° C. and 50-70% relative humidity and the test is evaluated after 3 weeks.

The herbicidal action is assessed using a linear nine-stage evaluation scale, wherein 1 stands for total damage of the test plants (100% herbicidal action) and 9 for no herbicidal action (The test plant grows like an untreated plant used as reference).

Results are compiled in table 13.

TABLE 13

| Compound No. | pre emergent herbicidal action at 4 kg/ha. | | | |
|---|---|---|---|---|
| | Avena | Sinapis | Setaria | Stellaria |
| 1.03 | 2 | 1 | 1 | 1 |
| 1.04 | 3 | 1 | 1 | 1 |
| 1.05 | 2 | 1 | 1 | 1 |
| 1.06 | — | 1 | 1 | 1 |
| 1.08 | — | — | 1 | 1 |
| 1.17 | — | 1 | 1 | 1 |
| 1.18 | — | — | 1 | 1 |
| 1.20 | — | — | 1 | 1 |

EXAMPLE B2

Post-emergence herbicidal action

A number of weeds, both monocotyledons and dicotyledons, are sprayed after emergence (at the 4- to 6-leaf stage) with an aqueous dispersion of active ingredient at a rate of 4 kg of active ingredient per hectare and kept at 24°-26° C. and 45-60% relative humidity. 15 days after the treatment the test is evaluated. The herbicidal action is assessed according to the scheme described in Example B1.

The test results are compiled in Table 5.

TABLE 14

| Compound No. | post emergent herbicidal action at 4 kg/ha. | | | | | | |
|---|---|---|---|---|---|---|---|
| | Avena | Setaria | Lolium | Solanum | Sinapis | Stellaria | Phaseolus |
| 1.03 | 2 | 2 | 1 | 1 | 1 | 1 | 1 |
| 1.04 | 1 | 1 | 1 | 1 | 1 | 1 | 1 |
| 1.05 | 1 | 1 | 1 | 1 | 1 | 1 | 1 |
| 1.06 | 1 | 1 | 1 | 1 | 1 | 1 | 1 |
| 1.08 | 2 | 1 | 1 | 1 | 1 | 1 | 1 |
| 1.17 | 2 | 2 | 1 | 1 | 1 | 1 | 1 |
| 1.18 | 1 | 1 | 1 | 1 | 1 | 1 | 1 |
| 1.20 | — | 3 | 1 | 1 | 1 | 1 | — |
| 4.10 | — | — | 2 | 1 | 1 | 2 | 1 |

EXAMPLE B3

Herbicidal action in paddy

The water weeds Echinochloa crus galli and Monocharia vag. are sown in plastics beakers (60 cm surface area, 500 ml volume). After sowing, the beakers are filled to the soil surface with water. 3 days after sowing, the water level is raised to slightly above (3-5 mm) the surface of the soil. Application is carried out 3 days after sowing by spraying an aqueous emulsion of the test substances onto the vessels at a rate of application of 250 g of active ingredient per hectare. The plant beakers are then placed in a greenhouse under optimum growth conditions for the rice weeds, i.e. at 25°-30° C. and high humidity. The tests are evaluated 3 weeks after the application.

The herbicidal action is assessed according to the scheme given in Example B1.

The test results are compiled in Table 15.

TABLE 15

| Compound No. | Echinochloa | Monocharia |
|---|---|---|
| 1.03 | 1 | 1 |
| 1.04 | 1 | 1 |
| 1.05 | 1 | 1 |
| 1.06 | 1 | 1 |
| 1.08 | 1 | 1 |
| 1.17 | 1 | 1 |
| 1.20 | 1 | 1 |
| 4.10 | 3 | 1 |

EXAMPLE B4

Pre-emergence herbicidal action

In a greenhouse, immediately after sowing the test plants in seed trays the surface of the soil is treated with an aqueous dispersion of the test compound. Various rates of application of active ingredient/hectare are tested. The seed trays are kept in the greenhouse at 22°-25° C. and 50-70% relative humidity and the test is evaluated after 3 weeks.

The herbicidal action is assessed according to a linear nine-stage evaluation scale (as described in Example B1) in comparison to not treated control plants.

Ratings of 1 to 4 (especially 1 to 3) indicate a good to very good herbicidal action. Ratings of 6 to 9 (especially 7 to 9) indicate a good tolerance (especially in the case of crop plants). Test results for compounds 1.03 and 1.17 are compiled in Table 16.

TABLE 16

| | Compound No. | | | | | |
|---|---|---|---|---|---|---|
| | 1.03 | | | 1.17 | | |
| | application rate [g/ha] | | | | | |
| | 1000 | 500 | 250 | 1000 | 500 | 250 |
| barley | 6 | 8 | 9 | 9 | 9 | 9 |
| wheat | 6 | 8 | 9 | 9 | 9 | 9 |
| maize | 7 | 8 | 9 | 7 | 8 | 9 |
| sorghum hybr. | 8 | 9 | 9 | 6 | 7 | 9 |
| rice (dry) | 7 | 8 | 9 | 6 | 8 | 9 |
| rottboellia ex. | 1 | 1 | 1 | 6 | 8 | 9 |
| soya | 9 | 9 | 9 | 9 | 9 | 9 |
| cotton | 7 | 9 | 9 | 9 | 9 | 9 |
| sun-flower | 8 | 9 | 9 | 9 | 9 | 9 |
| abutilon | 1 | 1 | 1 | 1 | 1 | 4 |
| sida spinosa | 1 | 2 | 3 | 3 | 3 | 4 |
| amaranthus ret. | 1 | 1 | 1 | 1 | 5 | 7 |

TABLE 16-continued

| | Compound No. | | | | | |
|---|---|---|---|---|---|---|
| | 1.03 | | | 1.17 | | |
| | application rate [g/ha] | | | | | |
| | 1000 | 500 | 250 | 1000 | 500 | 250 |
| chenopodium sp. | 1 | 1 | 1 | 1 | 1 | 1 |
| solanum nigrum | 1 | 1 | 1 | 1 | 1 | 1 |
| chrysanthe. leuc. | 1 | 1 | 1 | 1 | 1 | 2 |
| viola tricolor | 1 | 1 | 1 | 1 | 1 | 1 |
| veronica sp. | 1 | 1 | 1 | 1 | 1 | 1 |

EXAMPLE B5

Post-emergence herbicidal action

A number of weeds, both monocotyledons and dicotyledons, are sprayed after emergence (at the 4- to 6-leaf stage) with an aqueous dispersion of active ingredient at a rate of 250 g to 1 kg of active ingredient per hectare and kept at 24°–26° C. and 45–60% relative humidity. 15 days after the treatment the test is evaluated in accordance with the evaluation scheme described in Example b1.

The test results for compound 1.03 and 1.17 are compiled in Table 17.

TABLE 17

| | Compound No. | | | | | | | | | | | |
|---|---|---|---|---|---|---|---|---|---|---|---|---|
| | 1.03 | | | | | | 1.17 | | | | | |
| | application rate [g/ha] | | | | | | | | | | | |
| | 1000 | 500 | 250 | 125 | 60 | 30 | 1000 | 500 | 250 | 125 | 60 | 30 |
| barley | 4 | 5 | 6 | 7 | 8 | 8 | 5 | 6 | 7 | 8 | 8 | 8 |
| wheat | 4 | 5 | 6 | 7 | 8 | 8 | 6 | 7 | 8 | 8 | 9 | 9 |
| maize | 3 | 4 | 6 | 7 | 8 | 9 | 4 | 4 | 5 | 7 | 8 | 9 |
| sorghum hybr. | 4 | 5 | 6 | 7 | 8 | 8 | 7 | 7 | 8 | 8 | 9 | 9 |
| abutilon | 1 | 1 | 1 | 1 | 1 | 1 | 1 | 1 | 1 | 1 | 1 | 1 |
| sida spinosa | 1 | 1 | 1 | 1 | 4 | 5 | 1 | 1 | 2 | 3 | 4 | 6 |
| xanthium sp. | 1 | 1 | 1 | 1 | 1 | 2 | 1 | 1 | 1 | 1 | 4 | 4 |
| amaranthus ret. | 1 | 1 | 1 | 1 | 1 | 4 | 1 | 1 | 1 | 4 | 4 | 4 |
| chenopodium sp. | 1 | 1 | 1 | 1 | 1 | 1 | 1 | 1 | 1 | 1 | 1 | 2 |
| solanum nigrum | 1 | 1 | 1 | 1 | 1 | 1 | 1 | 1 | 1 | 1 | 1 | 1 |
| ipomoea | 1 | 1 | 1 | 1 | 1 | 4 | 1 | 1 | 1 | 1 | 4 | 4 |
| sinapis | 1 | 1 | 1 | 1 | 1 | 4 | 1 | 2 | 3 | 4 | 5 | 6 |
| chrysanthe. leuc. | 1 | 1 | 1 | 1 | 4 | 5 | 1 | 1 | 1 | 2 | 4 | 6 |
| viola tricolor | 1 | 1 | 1 | 1 | 1 | 1 | 1 | 1 | 1 | 1 | 1 | 1 |
| veronica sp. | 1 | 1 | 1 | 1 | 1 | 2 | 1 | 1 | 1 | 1 | 4 | 6 |

We claim:

1. A 4,5,6,7-tetrahydro-indazole of the formula Ic

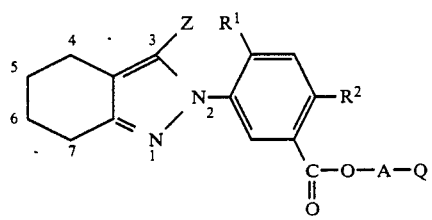

wherein
$R^1$ is hydrogen or halogen,
$R^2$ is halogen,
A is a straight or branched $C_1$–$C_4$ alkylene chain,
Q is —S(O)$_m$—$R^3$, di-$C_1$–$C_4$-alkylamino, a 5- or 6-membered heterocyclic ring selected from the group consisting of pyridin-2-yl, 1,3-thiazol-5-yl, thiophen-2-yl, pyrrolidin-2-on-1-yl, pyrrolidin-1-yl, morpholin-4-yl, furan-2-yl, pyrrol-1-yl, imidazol-1-yl, pyrazol-1-yl and 1,2,4-triazol-1-yl, which is unsubstituted or mono- or di-substituted by $C_1$–$C_4$- alkyl, or
—A—Q is 2-(1H-indol-1-yl)ethyl

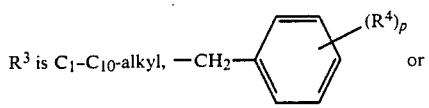

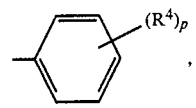

m is zero, 1 or 2,
$R^4$ is $C_1$–$C_4$-alkyl, halogen or $C_1$–$C_4$-alkoxy,
p is zero, 1, 2 or 3,
Z is halogen, methyl, $C_1$–$C_6$-alkoxy or $C_1$–$C_6$-alkylthio, or an agrochemically acceptable salt with an acid or base.

2. A 4,5,6,7-tetrahydro-indazole of the formula Ic

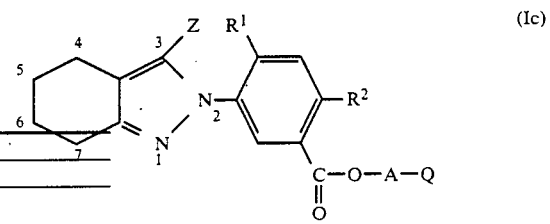

wherein
$R^1$ is hydrogen, fluorine or chlorine,
$R^2$ is fluorine, chlorine or bromine,
A is a straight-chain or branched $C_1$–$C_4$-alkylene chain,
Q is $C_1$–$C_{10}$-alkylthio, —S(O)$_m$$R^3$ or di-$C_1$–$C_4$-alkylamino,

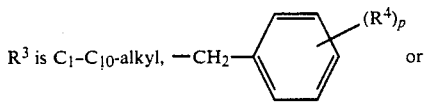

-continued

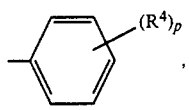

m is zero, 1 or 2, $R^4$ is $C_1-C_4$-alkyl, fluorine, chlorine, bromine or $C_1-C_4$-alkoxy, Z is chlorine, bromine, methyl, $C_1-C_6$-alkoxy or $C_1-C_6$-alkylthio, or an agrochemically acceptable salt with an acid or base.

3. A compound of the formula Ic according to claim 2, wherein $R^2$ is chlorine or bromine, A is ethano, 1-methylethano, 2-methylethano or propano, Q is $C_1-C_6$-alkylthio or $-S(O)_mR^3$, $R^3$ is benzyl or phenyl, m is zero, 1 or 2, and Z is chlorine or methyl.

4. A compound of the formula Ic according to claim 2, wherein Q is $C_1-C_6$-alkylthio.

5. A compound of the formula Ic according to claim 2, wherein Q is di-$C_1-C_4$-alkylamino.

6. A compound of the formula Ic according to claim 2, wherein $R^1$ is fluorine and $R^2$ is chlorine or bromine.

7. A compound of the formula Ic according to claim 2, wherein Z is chlorine or methyl, $$A \text{ is } -CH_2-CH_2- \text{ or } -\underset{\underset{CH_3}{|}}{CH}-CH_2-, \text{ and}$$

Q is $C_1-C_6$-alkylthio.

8. A compound of the formula Ic according to claim 2, wherein Z is chlorine or methyl, $$A \text{ is } -CH_2-CH_2- \text{ or } -\underset{\underset{CH_3}{|}}{CH}-CH_2-,$$

Q is $C_1-C_6$-alkylthio, $R^1$ is fluorine, and $R^2$ is chlorine or bromine.

9. A compound according to claim 2, selected from the group consisting of 3-chloro-2-{4-chloro-2-fluoro-5-[1-methyl-2-(1-methylethylthio)-ethoxycarbonyl]-phenyl}-4,5,6,7-tetrahydro-2H-indazole, 3-chloro-2-[4-chloro-2-fluoro-5-(1-dimethylamino-1-methylethoxycarbonyl)-phenyl]-4,5,6, 7-tetrahydro-1H-indazole and 3-chloro-2-[4-chloro-2-fluoro-5-(2-ethylthio-1-methylethoxycarbonyl)-phenyl]-4,5,6,7-te trahydro-2H-indazole.

10. A herbicidal composition which comprises, besides an inert carrier or other adjuvant, as active ingredient, a herbicidally effective amount of a compound according to claim 2.

11. A method for controlling undesired plant growth, which comprises treating the undesired plant or its living area with a herbicidally effective amount of a compound according to claim 2.

12. A method for controlling undesired weed growth in cultures of crop plants, which comprises treating the crop or the crop area pre- or post emergence with a herbicidally effective amount of a compound according to claim 2.

13. A method according to claim 12 wherein the crop plants are barley, wheat, maize, rice, sorghum, soya, cotton, or sunflower plants.

14. A method for controlling undesired weed growth in cultures of crop plants which comprises treating seeds of said crop plants with a herbicidally effective amount of a compound according to claim 2 prior to planting.

15. A herbicidal composition which comprises a herbicidally effective amount of a compound according to claim 1 and a carrier.

16. A method for controlling undesired plant growth which comprises treating the undesired plant or its living area with a herbicidally effective amount of a compound according to claim 1.

* * * * *